(12) United States Patent
Lee et al.

(10) Patent No.: US 11,406,911 B2
(45) Date of Patent: Aug. 9, 2022

(54) DISPERSION PLATE AND PURIFICATION COLUMN INCLUDING THE SAME

(71) Applicant: LG CHEM, LTD., Seoul (KR)

(72) Inventors: Junyoung Lee, Daejeon (KR); Youngsoo Song, Daejeon (KR); Gyu Chul Do, Daejeon (KR); Ye Hoon Im, Daejeon (KR); Dong Rak Son, Daejeon (KR)

(73) Assignee: LG CHEM, LTD., Seoul (KR)

( * ) Notice: Subject to any disclaimer, the term of this patent is extended or adjusted under 35 U.S.C. 154(b) by 408 days.

(21) Appl. No.: 16/625,565

(22) PCT Filed: Jul. 5, 2018

(86) PCT No.: PCT/KR2018/007650
§ 371 (c)(1),
(2) Date: Dec. 20, 2019

(87) PCT Pub. No.: WO2019/009647
PCT Pub. Date: Jan. 10, 2019

(65) Prior Publication Data
US 2021/0339162 A1 Nov. 4, 2021

(30) Foreign Application Priority Data
Jul. 7, 2017 (KR) .......................... 10-2017-0086529

(51) Int. Cl.
*C07C 7/148* (2006.01)
*B01D 3/00* (2006.01)

(52) U.S. Cl.
CPC ............. *B01D 3/008* (2013.01); *B01D 3/009* (2013.01); *C07C 7/148* (2013.01)

(58) Field of Classification Search
None
See application file for complete search history.

(56) References Cited

U.S. PATENT DOCUMENTS

| | | | |
|---|---|---|---|
| 3,796,657 A * | 3/1974 | Pretorius et al. | .. G01N 27/4045 73/23.39 |
| 4,526,757 A | 7/1985 | Gupta | |
| 5,799,877 A | 9/1998 | Gupta et al. | |
| 5,942,197 A | 8/1999 | Gupta et al. | |
| 6,093,373 A | 7/2000 | Darmancier et al. | |
| 6,221,117 B1 * | 4/2001 | Edlund | .................... B01J 8/006 422/106 |
| 6,613,219 B2 | 9/2003 | Harter et al. | |
| 8,205,863 B2 | 6/2012 | Monkelbaan | |

(Continued)

FOREIGN PATENT DOCUMENTS

| | | |
|---|---|---|
| CN | 2688707 Y | 3/2005 |
| CN | 206045985 U | 3/2017 |

(Continued)

*Primary Examiner* — Tam M Nguyen
(74) *Attorney, Agent, or Firm* — Dentons US LLP

(57) ABSTRACT

Disclosed is a dispersion plate for a purification column including a support plate, at least one first fluid tube penetrating through the support plate, and a plurality of second fluid tubes arranged to be spaced apart from the first fluid tube and surround the first fluid tube, wherein a length of at least one of the second fluid tubes is longer than lengths of another second fluid tubes, and is shorter than or equal to a length of the first fluid tube.

10 Claims, 10 Drawing Sheets

(56) References Cited

U.S. PATENT DOCUMENTS

| | | | |
|---|---|---|---|
| 2001/0055548 A1* | 12/2001 | Harter | B01J 8/008 422/139 |
| 2003/0181772 A1 | 9/2003 | Meyer et al. | |
| 2005/0062178 A1* | 3/2005 | Harter | B01J 8/025 261/96 |
| 2006/0163758 A1 | 7/2006 | Muller | |
| 2008/0202424 A1 | 8/2008 | Pozzetti et al. | |
| 2009/0174091 A1* | 7/2009 | Jarlkov | B01D 3/26 261/114.5 |
| 2010/0015018 A1 | 1/2010 | Augier et al. | |
| 2012/0014849 A1 | 1/2012 | Killen et al. | |
| 2013/0082125 A1 | 4/2013 | Akin et al. | |
| 2016/0082364 A1 | 3/2016 | Haroun et al. | |
| 2016/0107099 A1 | 4/2016 | Haroun et al. | |
| 2016/0175733 A1 | 6/2016 | Haroun et al. | |
| 2017/0158583 A1 | 6/2017 | Heida et al. | |
| 2019/0314736 A1* | 10/2019 | Chen | B01J 19/32 |
| 2021/0146273 A1* | 5/2021 | Fourati | B01D 1/0005 |

FOREIGN PATENT DOCUMENTS

| | | |
|---|---|---|
| JP | 9-225290 A | 9/1997 |
| JP | 2002-507149 A | 3/2002 |
| JP | 2004-514647 A | 5/2004 |
| JP | 2010024451 A | 2/2010 |
| JP | 2013538116 A | 10/2013 |
| JP | 2016-120485 A | 7/2016 |
| JP | 2016-523179 A | 8/2016 |
| KR | 10-0741214 B1 | 12/2002 |
| KR | 10-0741214 B1 | 7/2007 |
| KR | 10-0770616 B1 | 10/2007 |
| KR | 10-2008-0032021 A | 4/2008 |
| KR | 10-2013-0064996 A | 6/2013 |
| KR | 10-2017-0028964 A | 3/2017 |
| KR | 10-2017-0055124 A | 5/2017 |
| WO | 2015/076427 A1 | 5/2015 |

* cited by examiner

DISPERSION PLATE AND PURIFICATION COLUMN INCLUDING THE SAME

The present application is a National Phase entry pursuant to 35 U.S.C § 371 of International Application No. PCT/KR2018/007650 filed on Jul. 5, 2018, and claims priority to and the benefit of Korean Patent Application No. 10-2017-0086529 filed in the Korean Intellectual Property Office on Jul. 7, 2017, the entire contents of which are incorporated herein by reference.

FIELD

The present invention relates to a dispersion plate, and particularly, to a dispersion plate used in a butadiene purification column.

BACKGROUND

Butadiene has been used as an intermediate of numerous petrochemicals such as synthetic rubber and electronic materials, which is one of the most important basic oils in a petrochemical market, and the demand and value thereof has been gradually increasing.

Butadiene may be obtained by purifying butadiene in a C4 mixture. For purification, a first extraction system, a second extraction system, and a purification system are included.

Here, in the purification system, a process of removing impurities is performed in order to increase the purity of butadiene, which is carried out in a purification column.

The purification column includes a dispersion plate and a catalyst layer therein, wherein steam injected from a lower portion thereof moves to an upper portion thereof, butadiene injected from the upper portion thereof moves to the lower portion thereof, and in the catalyst layer, a reaction for removing impurities occurs.

Here, the dispersion plate separates the flow of steam and butadiene from each other, such that the purification is performed efficiently.

The dispersion plate includes a plurality of tubes through which butadiene and steam flow, and some of the tubes through which butadiene flows may be clogged by a popcorn-type impurity (hereinafter, referred to as a popcorn polymer) produced during the process.

As such, when some of the tubes are clogged, the dispersion plate fails to function, a liquid level of butadiene rises, so that butadiene flows in the tube through which steam flows, thereby reducing purification efficiency.

SUMMARY

The present invention has been made in an effort to provide a dispersion plate for butadiene purification column in which purification efficiency is not reduced even if some of the tubes through which butadiene is discharged are clogged to cause a rise in liquid level, and a purification column including the same.

An exemplary embodiment of the present invention provides a dispersion plate for a purification column including a support plate, at least one first fluid tube penetrating through the support plate, and a plurality of second fluid tubes arranged to be spaced apart from the first fluid tube and surrounding the first fluid tube, wherein a length of at least one of the second fluid tubes is longer than a length of another of the second fluid tubes, and is shorter than or equal to a length of the first fluid tube.

The second fluid tubes may be arranged at a predetermined intervals along a circumference of the first fluid tube.

The second fluid tubes may include a tube having a first length and a tube having a second length longer than the first length, wherein the first length tube and the second length tube are alternately arranged along the circumference of the first fluid tube.

Each of the second fluid tubes may have an elliptical inlet in which a first end point positioned to be spaced apart from one surface of the support plate by a first distance, and a second end point positioned to be spaced apart from the one surface of the support plate by a second distance longer than the first distance are connected to each other.

The second end point of the first tube may be positioned on the same line as the first end point of the second tube.

Diameters of the first length tube and the second length tube may be the same.

The second fluid tubes may include a plurality of first length tubes surrounding the first fluid tube, arranged at a predetermined interval, and having the same length; and a plurality of second length tubes each positioned between adjacent first length tubes and having different lengths, wherein a length of the second length tubes are longer than a length of the first length tubes.

The first length tubes may be arranged at an angle in which the first fluid tube having a circular cross-section is evenly divided.

The second fluid tubes may include the same number of the first length tubes and the second length tubes.

Another embodiment of the present invention provides a purification column including a purification chamber having a lower portion into which steam is injected and an upper portion into which butadiene is injected, at least one dispersion plate installed across the inside of the purification chamber, and at least one catalyst layer positioned to be spaced apart from the dispersion plate and removing impurities of butadiene, wherein the dispersion plate includes a support plate, at least one first fluid tube penetrating through the support plate, and a plurality of second fluid tubes arranged to be spaced apart from the first fluid tube and surround the first fluid tube, a length of at least one of the second fluid tubes being longer than lengths of other second fluid tubes, and being shorter than or equal to a length of the first fluid tube.

According to an embodiment of the present invention, in the dispersion plate installed in the butadiene purification column, the butadiene tubes may have various lengths, whereby deterioration in purification efficiency may be minimized even if the tube is clogged due to a popcorn polymer.

DETAILED DESCRIPTION

Figure 1:
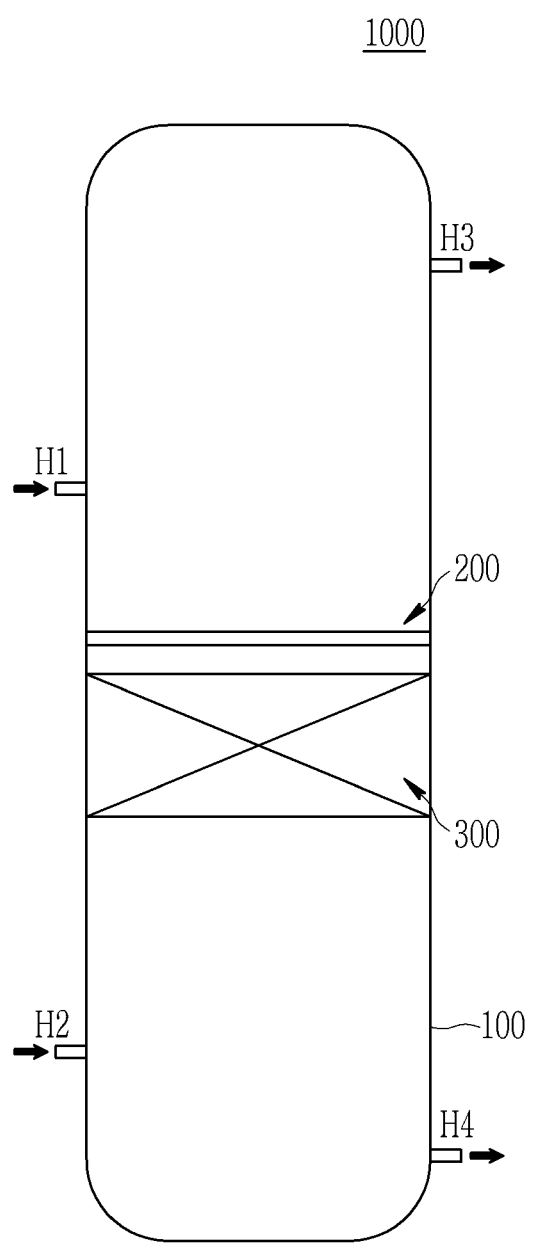
FIG. 1 is a schematic configuration diagram showing a purification column according to an exemplary embodiment of the present invention.

Hereinafter, exemplary embodiments of the present invention will be described in detail so as for those of ordinary skill in the art to easily implement, with reference to the accompanying drawings. The present invention may be embodied in many different forms and is not limited to the exemplary embodiments described herein.

To clarify the present invention, parts not related to the description are omitted from the drawings, and the same or similar components are denoted by the same reference numerals throughout the specification.

In addition, the size and thickness of each component shown in the drawings are arbitrarily shown for convenience of explanation, and thus the present invention is not necessarily limited to those shown in the drawings.

Throughout the specification, when referring that a certain element is "connected" to another element, it includes not only "directly connected" but also "indirectly connected" between other members. In addition, when referring that a certain element "comprises" a certain component, this means that the element may further include another components instead of excluding another components, unless explicitly described to the contrary.

Hereinafter, with reference to the accompanying drawings, a dispersion plate installed in a butadiene purification column according to an exemplary embodiment of the present invention will be described in detail.

FIG. 1 is a schematic configuration diagram showing a purification column according to an exemplary embodiment of the present invention.

Purification of butadiene according to an exemplary embodiment of the present invention is performed in the purification column. As shown in FIG. 1, a purification column 1000 according to an exemplary embodiment of the present invention includes a purification chamber 100, a dispersion plate 200 installed across the purification chamber 100, inlets H1 and H2 and outlets H3 and H4 for injecting and discharging fluid into/from the purification chamber 100, and a catalyst layer 300 for removing impurities.

The purification chamber 100 provides a space in which butadiene is purified by reacting with a catalyst and separated from an external environment.

The purification chamber 100 includes a first inlet H1 through which butadiene is supplied, a second inlet H2 through which steam is injected, a first outlet H3 through which steam is discharged, and a second outlet H4 through which purified butadiene is discharged.

The first inlet H1 is positioned at an upper portion of the purification chamber, and the second outlet H4 is positioned at a lower portion of the purification chamber to allow butadiene supplied from the upper portion of the purification chamber to the lower portion thereof and then purified to be discharged through the second outlet H4 at the lower portion thereof.

The second inlet H2 is positioned at the lower portion of the purification chamber, and the first outlet H3 is positioned at the upper portion of the purification chamber 100 to allow steam supplied to the lower portion of the purification chamber 100 and then moving to the upper portion of the purification chamber 100 to be discharged through the first outlet H3.

The catalyst layer 300 may be selected depending on the impurities to be removed from butadiene supplied, and may be a catalyst containing a metal.

The dispersion plate 200, which is to separate the catalyst layer 300, butadiene and steam from one another, is installed across the purification chamber 100.

Figure 2:
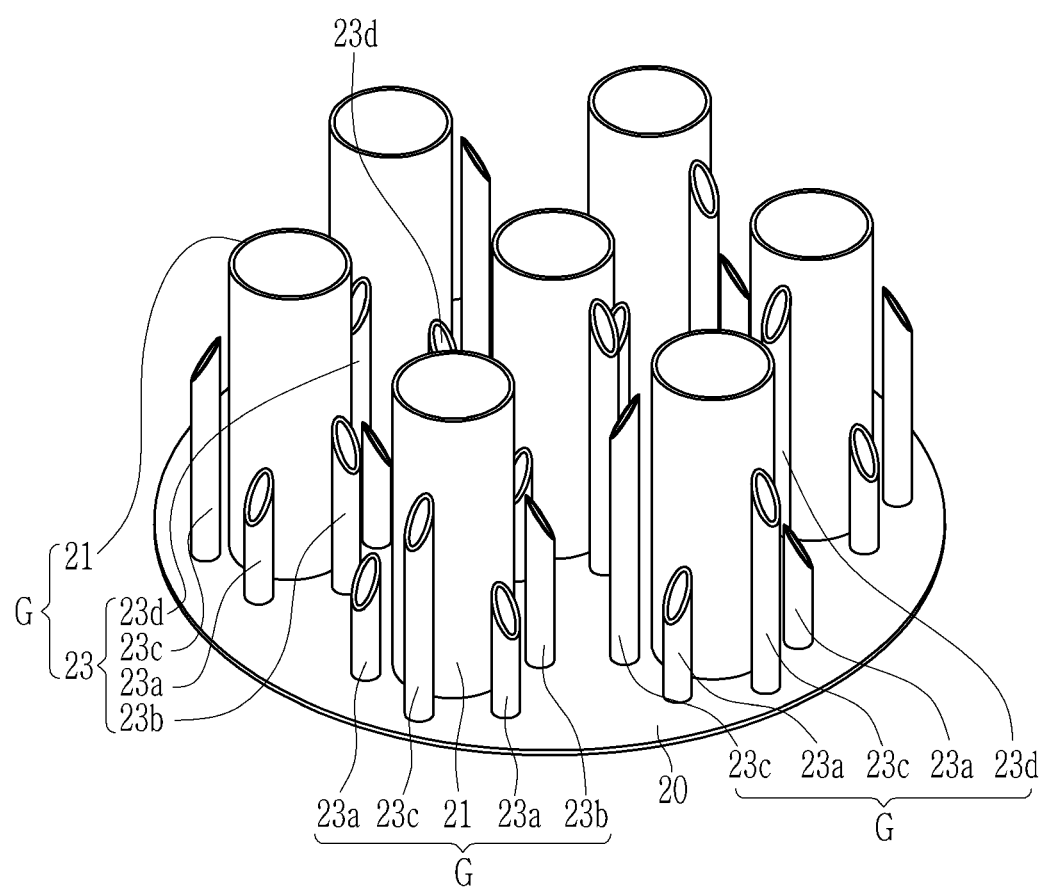
FIG. 2 is a schematic perspective diagram showing a dispersion plate according to an exemplary embodiment of the present invention.
Figure 3:
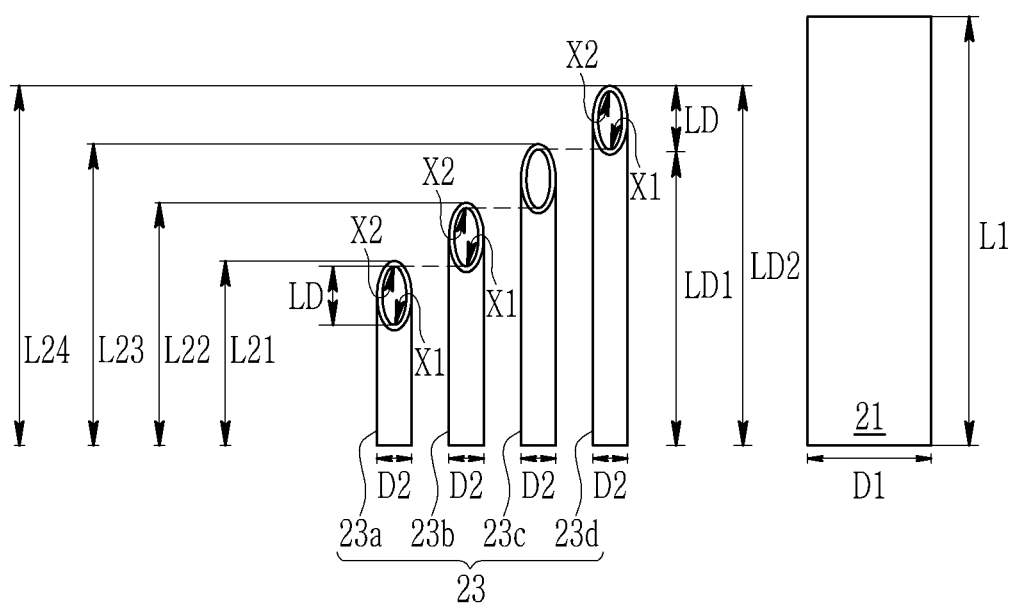
FIG. 3 is a diagram for comparing and illustrating a length of a fluid tube included in FIG. 2.
Figure 4:
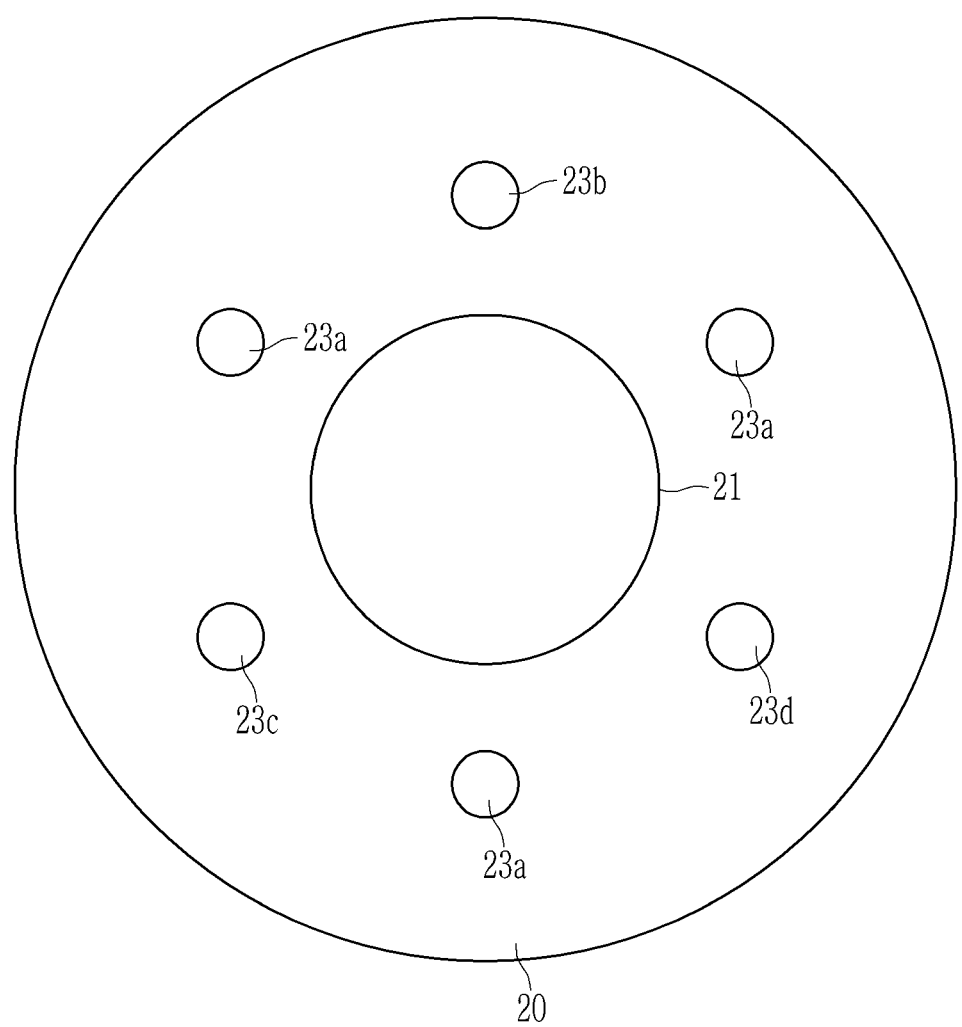
FIG. 4 is a layout diagram showing a fluid tube included in one unit group included in FIG. 2.

FIG. 2 is a schematic perspective diagram showing a dispersion plate according to an exemplary embodiment of the present invention. FIG. 3 is a diagram for comparing and illustrating a length of a fluid tube included in FIG. 2. FIG. 4 is a layout diagram showing a fluid tube included in one unit group included in FIG. 2.

Referring to FIG. 2, the dispersion plate 200 may include a support plate 20, at least one first fluid tube 21 penetrating through the support plate 20, and a plurality of second fluid tubes 23 arranged to be spaced apart from the first fluid tube 21 and surround the first fluid tube 21. Here, the second fluid tubes 23 may be arranged, at a predetermined interval, along the circumference of the first fluid tube 21.

Vapor (steam) may flow through the first tube 21 and butadiene may flow through the second fluid tube 23.

Referring to FIG. 3, a diameter D1 of the first tube 21 may be larger than a diameter D2 of the second fluid tubes 23. A length of the second fluid tube 23 may be shorter than a length of the first fluid tube 21 and a length of at least one of the second fluid tubes 23 may be longer than a length of another second fluid tube 23, but is not limited thereto, and three, four, or more second fluid tubes having different lengths may be formed.

Hereinafter, the second fluid tubes having four different lengths will be described as an example. For convenience of explanation, among the second fluid tubes having different lengths, the second fluid tube having the shortest length is referred to as a first tube 23a, and in order of increasing length, the second fluid tubes having different lengths, in the order of increasing lengths, are each referred to as a second tube 23b, a third tube 23c and a fourth tube 23d.

Referring to FIG. 2 and FIG. 3, the second fluid tube 23 is cut obliquely and an inlet of the second fluid tube 23 may have an elliptical inlet in which a first end point X1 positioned to be spaced apart from one surface of the support plate 20 by a first distance LD1, and a second end point X2 positioned to be spaced apart from the one surface of the support plate 20 by a second distance LD2 longer than the first distance LD1 are connected each other.

Here, the second end point X2 is positioned relatively adjacent to the first fluid tube 21, and the first end point is positioned relatively far from the first fluid tube 21. Therefore, the elliptical inlet of the second fluid tube 23 is arranged so as not to face the first fluid tube 21, thereby allowing butadiene to easily flow in. A difference between a length L21 of the first tube 23a and a length L22 of the second tube 23b, a difference between a length L22 of the second tube 23b and a length L23 of the third tube 23c, and a difference between a length L23 of the third tube 23c and a length L24 of the fourth tube 23d may be a difference LD (hereinafter, referred to as a height of the elliptical inlet) between the second distance LD2 and the first distance LD1, respectively.

Thus, the second end point X2 of the first tube 23a may be positioned on the same line as the first end point X1 of the second tube 23b, the second end point X2 of the second tube 23b may be positioned on the same line as the first end point X1 of the third tube 23c, and the second end point X2 of the third tube 23c may be positioned on the same line as the first end point X1 of the fourth tube 23d. That is, when arranging a second fluid tube having a longer length than a second fluid tube having a reference length, a second fluid tube having a longer length than a second fluid tube having the reference length (or previously arranged) by a height LD of the elliptical inlet may be arranged, and the second end point X2 of the second fluid tube having the reference length and the first end point X1 of the second fluid tube arranged thereafter may be arranged so as to be positioned on the same line.

Meanwhile, when the plurality of second fluid tubes 23 surrounding the first fluid tube 21 around one first fluid tube 21 are referred to as one unit group G, the dispersion plate 200 may include a plurality of unit groups G depending on a purification capacity of the purification column. For example, the dispersion plate 200 may include seven unit groups G, and, the unit group G may be arranged at a predetermined interval in the support plate.

Referring to FIG. 2 and FIG. 4, the second fluid tubes 23 having different lengths and included in the unit group G may include at least two second fluid tubes 23 having the same length. When one unit group G has six second fluid tubes, it may include three first tubes 23a and three second tubes 23b, respectively, and the first tubes 23a and the second tube 23b may be arranged alternately. Alternatively, one unit group G may include three first tubes 23a, one second tube 23b, one third tube 23c, and one fourth tube 23d, and the second tube 23b, the third tube 23c, and the fourth tube 23d may be arranged between adjacent first tubes 23a.

As in an exemplary embodiment of the present invention, when the second fluid tubes 23 through which the butadiene flows have various lengths, the function of the dispersion plate may be extended although some of the second fluid tubes 23 are clogged due to popcorn polymer necessarily produced in addition to butadiene.

Figure 5:
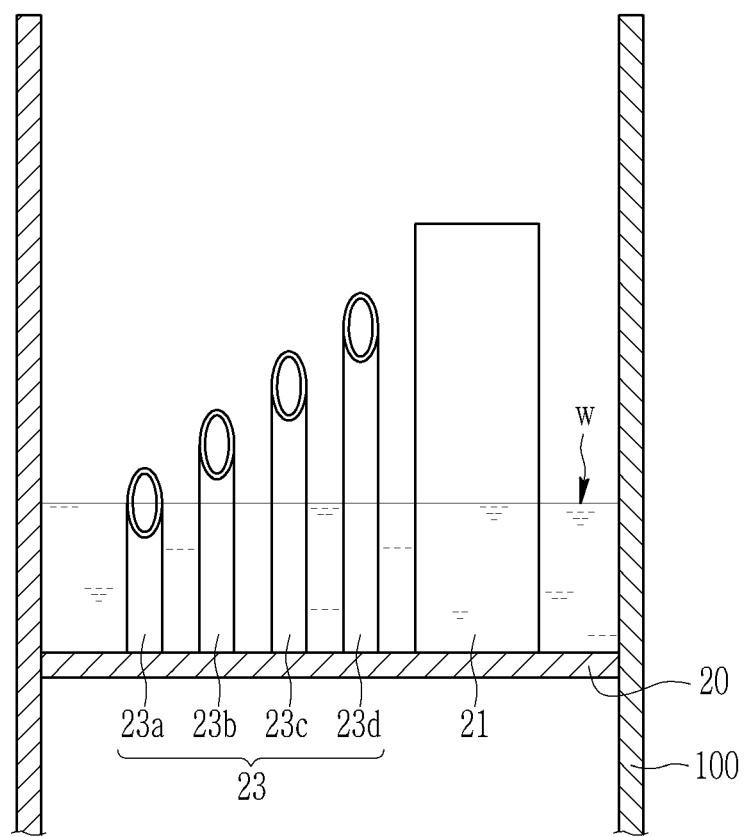
FIG. 5 to FIG. 7 are schematic diagrams for explaining a fluid flow in a dispersion plate according to an exemplary embodiment of the present invention.
Figure 6:
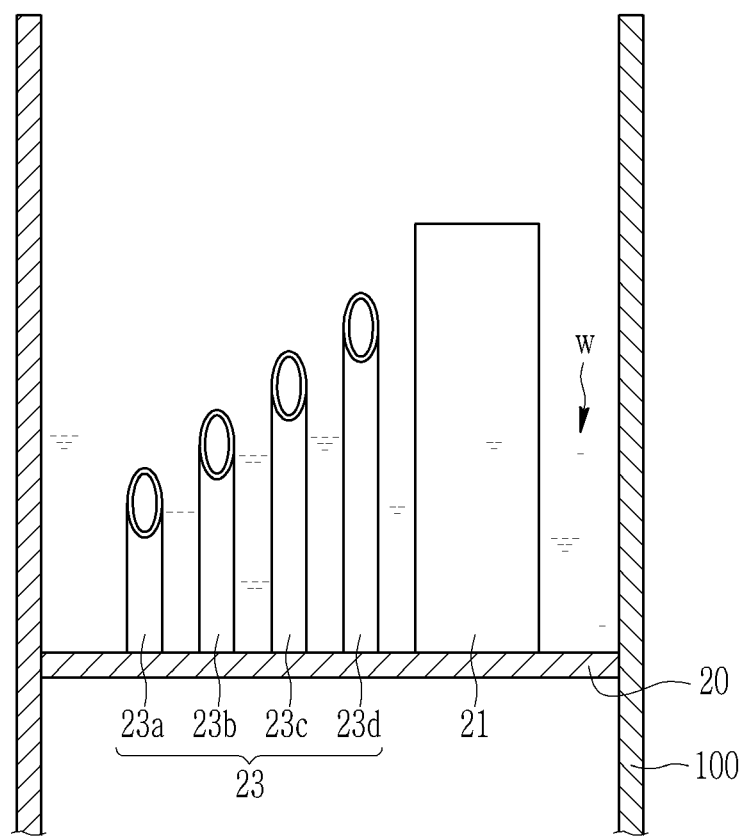
Figure 7:
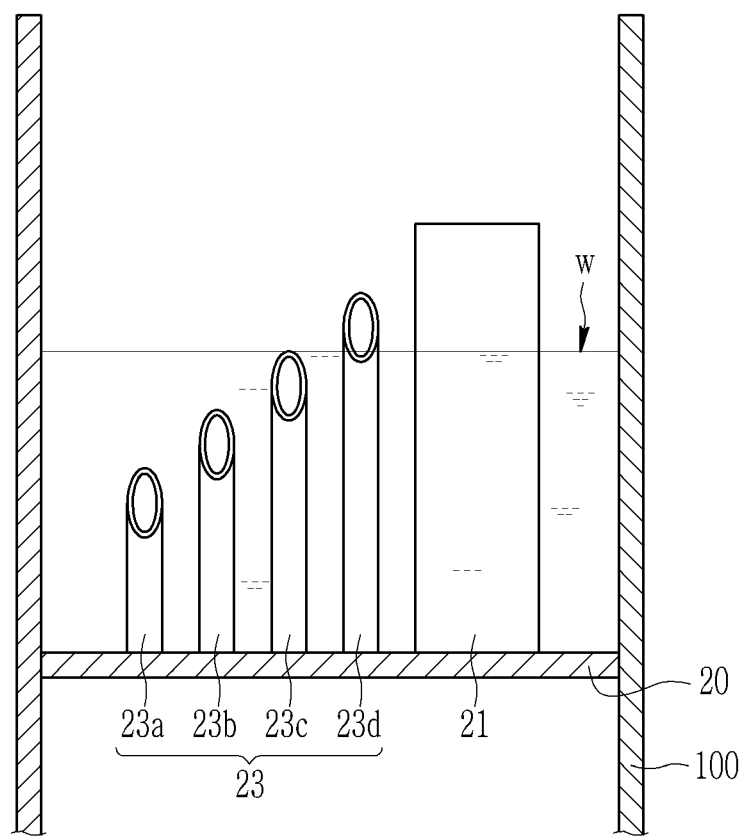

FIG. 5 to FIG. 7 are schematic diagrams for explaining a fluid flow in the dispersion plate according to an exemplary embodiment of the present invention. In order to assist in understanding of the invention, the fluid tubes arranged in the order of their lengths are shown.

Referring to FIG. 5, butadiene is supplied from the upper portion of the purification column and stored on the support plate 20, and when the butadiene reaches a predetermined level or more, it is transferred to the catalyst layer at the lower portion of the purification column, through the second fluid tubes 23.

Some of the plurality of second fluid tubes may be clogged by the popcorn polymer. Clogging due to the popcorn polymer results in a difference in a flux of the supplied butadiene and the butadiene discharged through the second fluid tube 23. Therefore, all of the supplied butadiene is not transferred to the catalyst layer but are stored, result in raising the height of the liquid level W of butadiene.

As in the present invention, when the second fluid tubes 23 are installed in multi-stages, butadiene is discharged through the tube 23a in the steady state. When some of the tube 23a is clogged, the liquid level W rises and, the liquid level W reaches the inlet of the tube 23b as shown in FIG. 6 and butadiene starts to be discharged through the tube 23b. For example, in the dispersion plate having seven groups, when two of the tubes 23a having a length of 120 mm are clogged, the liquid level height may be raised to 150 mm. Therefore, at the inlet of the tube 23b, the first end point may be positioned at 150 mm, which is the liquid level height.

Thereafter, when some of the tube 23b is also clogged, the liquid level W rises again, the liquid level W reaches the tube 23c as shown in FIG. 7, and then butadiene is discharged through the tube 23c. When some of the tube 23c is clogged and the liquid level continuously rises, butadiene is discharged through the tube 23d, and the discharging through the second fluid tubes may be performed sequentially until the liquid level reaches the first fluid tube.

Conventionally, when some of the plurality of second fluid tubes having the same length are clogged, the flux of butadiene supplied to the catalyst layer is small while the liquid level rises, thereby reducing purification efficiency. Also, butadiene, whose the liquid level height was rapidly raised, was discharged through the first fluid tube, and disturbed the movement of steam, thereby reducing purification efficiency.

However, in the present invention, butadiene may be discharged even while the liquid level rises and reaches the first fluid tube, thereby reducing the deterioration in purification efficiency.

In addition, in an exemplary embodiment of the present invention, the second end point X2 of a second fluid tube which relatively first starts to discharge (for example, tube 23a which starts to discharge prior to the tube 23b), and the first end point X1 of the tube 23b starting the next discharge may be positioned on the same line. Therefore, even if the liquid level rises, it is possible to perform a discharge immediately, thereby preventing the deterioration in the purification efficiency.

In addition, when the liquid level rises, the popcorn polymer together with butadiene may reach the catalyst layer through the first fluid tube, thereby reducing purification efficiency. However, in an exemplary embodiment of the present invention, the rise of the liquid level may delay as much as possible, thereby delaying the deterioration in purification efficiency due to the transfer of the popcorn polymer to the catalyst layer.

Figure 8:
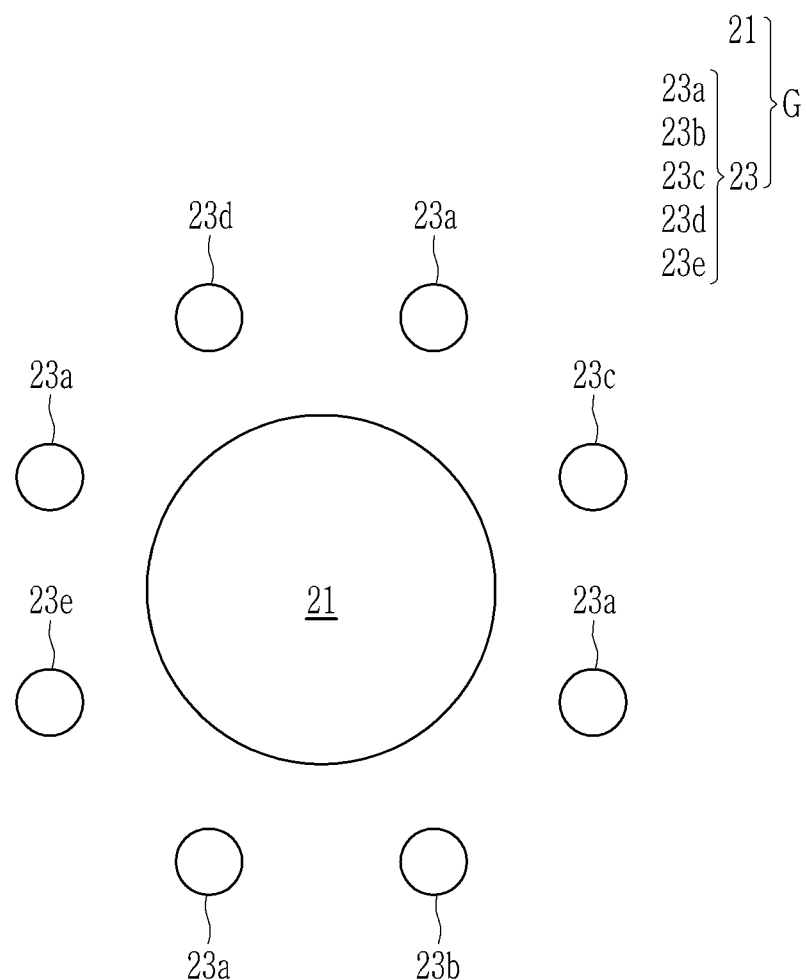
FIG. 8 is a schematic layout diagram showing a dispersion plate according to another embodiment of the present invention.
Figure 9:
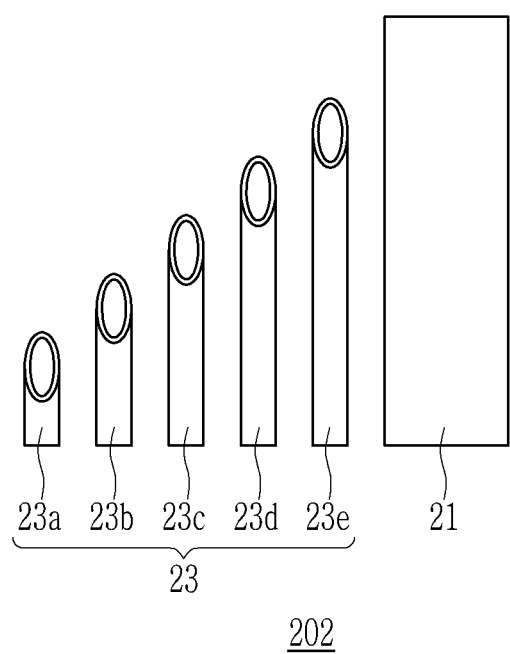
FIG. 9 is a diagram for comparing and illustrating a length of a fluid tube included in FIG. 8.

FIG. 8 is a schematic layout diagram showing a dispersion plate according to another embodiment of the present invention. FIG. 9 is a diagram for comparing and illustrating a length of a fluid tube included in FIG. 8.

The dispersion plate shown in FIG. 8 and FIG. 9 is mostly the same as that shown in FIG. 2 to FIG. 4, and thus only different parts will be described in detail. For convenience of explanation, one unit group is described as an example, and the dispersion plate may include a plurality of such unit groups I.

As shown in FIG. 8 and FIG. 9, a dispersion plate 202 may include the first fluid tube 21 and the second fluid tubes 23, and the second fluid tubes 23 may include tubes 23a, 23b, 23c, 23d, and 23e having different lengths, and may be installed in multi-stages.

The second fluid tubes 23 in FIG. 8 and FIG. 9 further includes one stage than the second fluid tube in FIG. 2 to FIG. 4. The reason may be that the distance from the tube 23a to the first fluid tube 21 is longer than the distance from the tube 23a to the first fluid tube 21 in FIG. 2 to FIG. 4, or the height LD of the inlet is short.

Here, the arrangement of the second fluid tubes in FIG. 2 to FIG. 4 and the second fluid tubes in FIG. 8 and FIG. 9 may be performed in the same manner.

That is, a reference tube is arranged at a predetermined interval along the circumference of the first fluid tube 21. Here, the reference tube may be tubes 23a, and all of the tubes 23a may have the same length and have the shortest length among the second fluid tubes.

The second fluid tubes may be arranged radially from the center of the first fluid tube. For example, in FIG. 3, since the number of the tube s23a, which is the reference tube, is three, the tubes 23a may be arranged at a position where the first fluid tube having a circular cross section is divided by 120 degrees. In FIG. 4, since the number of the tube 23a, which is the reference tube, is four, the tubes 23a may be arranged at a position where the first fluid tube having a circular cross section is divided by 90 degrees.

Intermediate tubes having longer lengths than the reference tube may be arranged between adjacent reference tubes, respectively. Here, the intermediate tubes may be the tube 23b, the tube 23c, the tube 23d, and the tube 23e, all of these lengths may be different.

In FIG. 4, the intermediate tubes having three different lengths may be arranged between adjacent reference tubes, respectively. In FIG. 8, the intermediate tubes having four different lengths may be arranged between adjacent reference tubes, respectively.

In an exemplary embodiment above, the second fluid tubes having four stages in FIG. 4 and five stages in FIG. 8 are each escribed as an example, but is not limited thereto, and may include more or fewer number of stages.

Since the reference tube may be arranged at an angle in which the first fluid tube having a circular cross-section is evenly divided, and the intermediate tubes may be arranged therebetween, the number of reference tubes and the number of intermediate tubes positioned between adjacent reference tubes may be the same.

Further, in exemplary embodiments of FIG. 4 and FIG. 8, one intermediate tube is described except for the reference tube, but is not limited thereto, and depending on the flux of butadiene, there may be multiple intermediate tubes in each stage.

Also, in an exemplary embodiment above, the first fluid tube having a circular cross-section is described as an example, but is not limited thereto. The first fluid tube may have various cross-sections, such as a tetragon and pentagon. Here, the second fluid tubes may be arranged radially at a predetermined angle from the center of the first fluid tube, while surrounding the first fluid tube.

Figure 10:
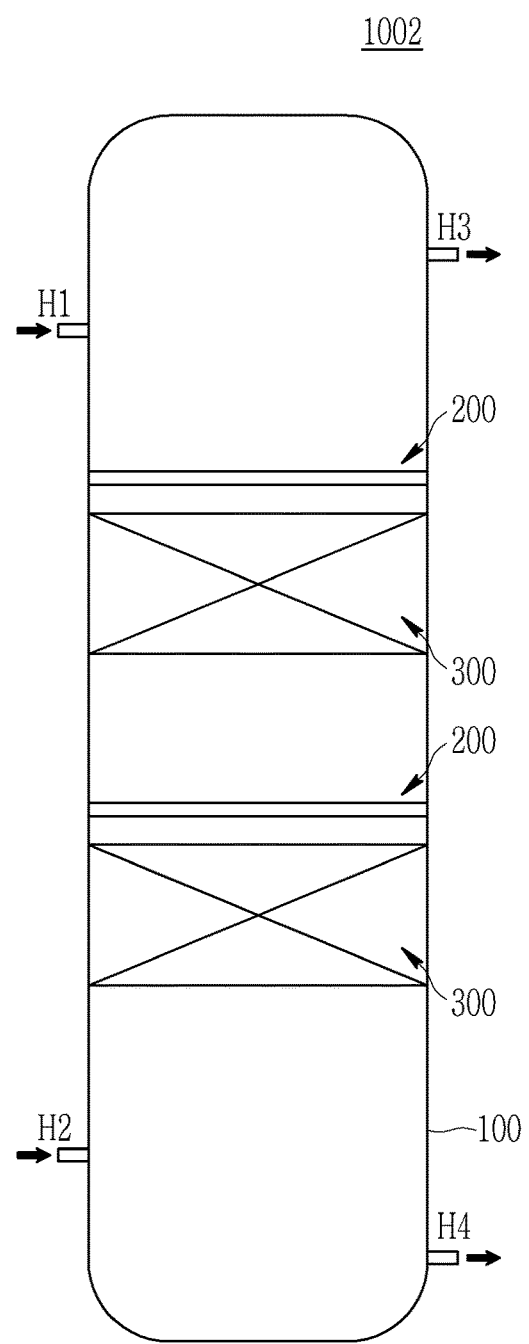
FIG. 10 is a schematic configuration diagram showing a purification column according to another embodiment of the present invention.

In an exemplary embodiment above, the purification column having one dispersion plate is described, but is not limited thereto, and as shown in FIG. 10, a plurality of dispersion plates may be installed, as necessary.

FIG. 10 is a schematic configuration diagram showing a purification column according to another embodiment of the present invention.

As shown in FIG. 10, a purification column 1002 may include two dispersion plates 200 and may be installed in the order of the catalyst layer 300, the dispersion plate 200, the catalyst layer 300, and the dispersion plate 200 from the lower portion of the purification column.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of symbols>

| 20: support plate | 21: first fluid tube |
|---|---|
| 23: second fluid tube | 100: purification chamber |
| 200, 202: dispersion plate | 300: catalyst layer |

-continued

<Description of symbols>

| 1000, 1002: purification column |
|---|
| H1, H2: inlet |
| H3, H4: outlet |

The invention claimed is:

1. A dispersion plate, comprising:
a support plate;
at least one first fluid tube penetrating through the support plate; and
a plurality of second fluid tubes arranged to be spaced apart from the first fluid tube and surround the first fluid tube,
wherein a length of at least one of the second fluid tubes is longer than a length of another second fluid tubes, and is shorter than or equal to a length of the first fluid tube.

2. The dispersion plate of claim 1, wherein:
the second fluid tubes are arranged at regular intervals along a circumference of the first fluid tube.

3. The dispersion plate of claim 2, wherein:
the second fluid tubes include
a first tube having a first length; and
a tube having a second length longer than the first length,
wherein the first length tube and the second length tube are alternately arranged along the circumference of the first fluid tube.

4. The dispersion plate of claim 3, wherein:
each of the second fluid tubes has an elliptical inlet in which a first end point positioned to be spaced apart from one surface of the support plate by a first distance, and a second end point positioned to be spaced apart from the one surface of the support plate by a second distance longer than the first distance are connected to each other.

5. The dispersion plate of claim 4, wherein:
the second end point of the first tube is positioned on the same line as the first end point of the second tube.

6. The dispersion plate of claim 3, wherein:
diameters of the first length tube and the second length tube are the same.

7. The dispersion plate of claim 1, wherein:
the second fluid tube includes
a plurality of first length tubes surrounding the first fluid tube, arranged at a predetermined interval, and having the same length; and
a plurality of second length tubes each positioned between adjacent first tubes and having different lengths,
wherein a length of the second length tubes are longer than a length of the first length tubes.

8. The dispersion plate of claim 7, wherein:
the first length tubes are arranged at an angle in which the first fluid tube having a circular cross-section is evenly divided.

9. The dispersion plate of claim 8, wherein:
the second fluid tube includes the same number of the first length tubes and the second length tubes.

10. A purification column, comprising:
a purification chamber having a lower portion into which steam is injected and an upper portion into which butadiene is injected;
at least one dispersion plate installed across the inside of the purification chamber; and at least one catalyst layer positioned to be spaced apart from the dispersion plate and removing impurities of butadiene,
wherein the dispersion plate includes
a support plate;
at least one first fluid tube penetrating through the support plate; and
a plurality of second fluid tubes arranged to be spaced apart from the first fluid tube and surround the first fluid tube, and
a length of at least one of the second fluid tubes being longer than lengths of other second fluid tubes, and being shorter than or equal to a length of the first fluid tube.

* * * * *